(12) United States Patent
del Soldato

(10) Patent No.: US 6,242,432 B1
(45) Date of Patent: Jun. 5, 2001

(54) ANTITHROMBOTIC ORGANIC NITRATES

(75) Inventor: Piero del Soldato, Milan (IT)

(73) Assignee: Nicox S.A., Paris (FR)

( * ) Notice: Subject to any disclaimer, the term of this patent is extended or adjusted under 35 U.S.C. 154(b) by 0 days.

(21) Appl. No.: 09/297,933

(22) PCT Filed: Nov. 12, 1997

(86) PCT No.: PCT/EP97/06311

§ 371 Date: May 11, 1999

§ 102(e) Date: May 11, 1999

(87) PCT Pub. No.: WO98/21193

PCT Pub. Date: May 22, 1998

(30) Foreign Application Priority Data

Nov. 14, 1996 (IT) .............................................. MI96A2368

(51) Int. Cl.[7] .......................... A61K 31/41; A61K 38/05; A61P 9/08; C07D 285/10; C07C 235/66

(52) U.S. Cl. .............................. 514/89; 514/91; 514/71; 514/211; 514/213; 514/298; 530/330; 530/331; 540/485; 540/523; 546/205; 548/400; 548/409; 548/452; 548/567

(58) Field of Search ...................................... 530/330, 331; 540/485, 523; 546/205; 548/400, 409, 452, 567; 514/89, 91, 71, 213, 398, 211

(56) References Cited

FOREIGN PATENT DOCUMENTS

| | | |
|---|---|---|
| WO 94/04484 | 3/1994 | (WO) . |
| WO 94/12463 | 6/1994 | (WO) . |
| WO 95/09831 | 4/1995 | (WO) . |
| WO 95/30641 | 11/1995 | (WO) . |

OTHER PUBLICATIONS

P. Del Soldato et al., *Journal of Pharmacology Methods*, 5, "The Anesthetized Guinea Pig as a Versatile Pharmacological" pp. 279–285 (1981).

A. Subissi et al., *Journal of Cardiovascular Pharmacology*, 20, "Pharmacology of Idrapril: A New Class of Angiotensin Converting Enzyme Inhibitors", pp. 139–146 (1992).

Miriam Oliveira Ribeiro et al., *Hypertension*, vol. 20, No. 3, "Chronic Inhibition of Nitric Oxide Synthesis, A New Model of Arterial Hypertension", pp. 298–303 (Sep. 1992).

Giuseppe Cirino et al., *Pergamon*, Thrombosis Research, vol. 79, No. 1, "Flurbinitroxybutylester: A Novel Anti-inflammatory Drug has Enhanced Antithrombotic Activity", pp. 73–81 (1995).

J.F. Pinon, *Journal of Pharmacological Methods*, 12, "In Vivo Study of Platelet Aggregation in Rats", pp. 79–84 (1984).

Goodman & Gilman's, McGraw–Hill, Health Professions Division, The Pharmacological Basis of Therapeutics, 9th Edition, pp. 1354–1357.

*Primary Examiner*—Mukund J. Shah
*Assistant Examiner*—Venkataraman Balasubramanian
(74) *Attorney, Agent, or Firm*—Arent, Fox Kintner Plotkin & Kahn

(57) ABSTRACT

Compounds or compositions containing compounds of the formula A-$(X_1-NO_2)_{to}$ or salts thereof, for the preparation of antithrombotic medications wherein "to" is the integer 1 or 2 $X_1$ is an alkylene connecting bridge and "A" is the residue of timolol or analapril.

15 Claims, No Drawings

ANTITHROMBOTIC ORGANIC NITRATES

The present invention relates to new products having an antithrombotic activity.

Cyclooxygenase (COX)-inhibiting anti-inflammatory products are known from previous patent applications in the name of the Applicant. See in particular the published patent applications WO 94/04484, WO 94/12463, WO 95/09831, WO95/30641. These patent applications referred to non-steroid anti-inflammatory products with a non-acid ending and to those with an acid ending mentioned as products known in the art.

Said products showed a much lower toxicity level compared to the reference products not containing group —$ONO_2$.

WO 95 30641 discloses compounds endowed with COX inhabiting activity and endowed with antithrombotic and antihypertensive activity.

EP 637583 concerns 1-anloxy-3-alkylamino-2-propanol nitrate esters of the general formula:

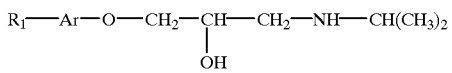

(I)

wherein $R_1$ is —$(CH_2)_m$—Z—$R_2$, m is 1 or 2, Z is —O— ether, —CONH amide or —COO— ester function and $R_2$ is a $C_{2-3}$ straight or branched chain alkyl having at least one nitroxy group. Said compounds are useful as drugs for the cardiovascular field.

WO 97 31896 discloses derivatives of formula:

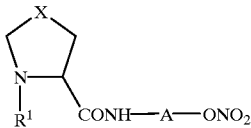

wherein X is —$CH_2$—, —O—, —S—; $R_1$ represents an alkanoyl group having one or more substituents. A represents alkylene or a group -B-D-E (where B and E may be the same or different and each represents a single bond or alkylene, and D represents cycloalkylene optionally substituted by aryl).

Said compounds have vasodilating and antianginal actions and are useful in the prophylaxis or treatment of angina pectoris.

The need for available products having an antithrombotic activity combined with lower toxicity in long term treatment was felt. In particular, the efficacy and safety of antithrombotic agents are closely related and research is aiming to find out new molecules with an increased therapeutic index, i.e. with improved efficacy and reduced toxicity (Goodman & Gilman: "The pharmacological basis of therapeutics", Ed. J. Hardman, L. Limbrid, Page 1357, 1996).

It was unexpectedly and surprisingly found that the products of the invention as defined below are effective in inhibiting platelet aggregation induced by different kinds of stimuli, in particular collagen and thrombin, and at the same time exhibit high safety in general, in particular a high gastric safety, without causing lesions to the gastro-intestinal mucosa in the treated animals.

The results of the present invention are much more surprising considering that the new classes of products of the invention are not cyclooxigenase (COX) inhibiting products and, therefore, they cannot be drawn in any way from the products described in the known art, in particular in the above patents.

A subject of the present invention are the compounds, or their compositions, of the general formula:

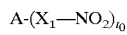

or their salts, for use as medicaments, in particular as antithrombotic agents since they are effective in inhibiting platelet aggregation, where:

$t_o$ is an integer equal to 1 or 2;

A=$RN_o$ where $N_o$=$(COX_u)_t$- or $COON_1$ where t is an integer equal to zero or 1; u is an integer equal to 0 or 1;

X=O, NH, $NR_{1c}$ where $R_{1c}$ is a linear or branched alkyl having from 1 to 10 carbon atoms; $N_1$ is a linear or branched alkyl having from 1 to 10 carbon atoms or hydrogen;

R is chosen from the following groups:

*Group A)

Ia)

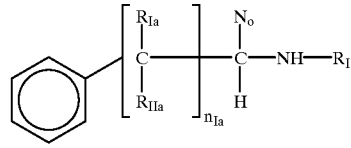

where $R_{Ia}$ and $R_{IIa}$ are equal or different one from the other and are H or a linear or whenever possible branched alkyl having from 1 to 3 C atoms, preferably $R_{Ia}$=$R_{IIa}$=H; $n_{Ia}$ is an integer from 1 to 6, preferably from 2 to 4; $R_I$ can be:

(X)

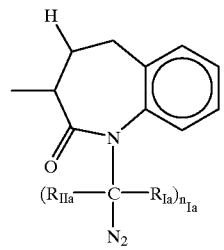

(XI)

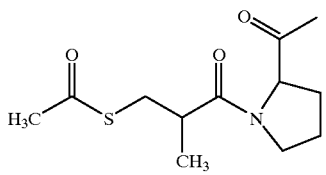

(XII)

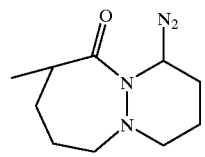

-continued (XIII)

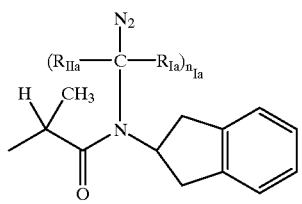

(XIV)

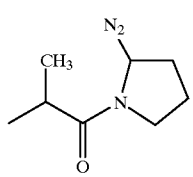

(XV)

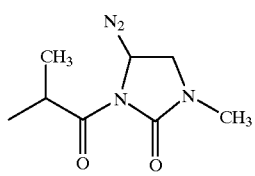

(XVI)

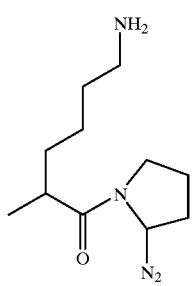

(XVII)

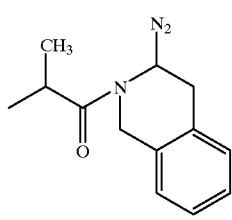

(XVIII)

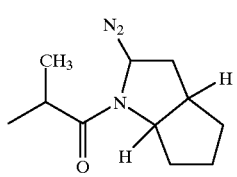

(XIX)

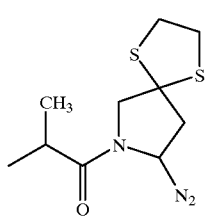

(XX)

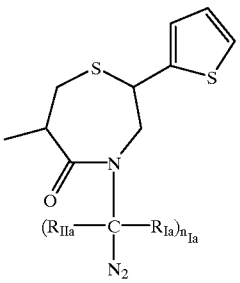

(XXI)

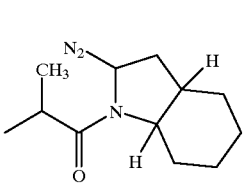

where $N_2$ has the same meaning as $N_o$; at least one of the groups $N_o$ or $N_2$ having one free valence capable of binding to $X_1$, (that is, t=1), Ib)

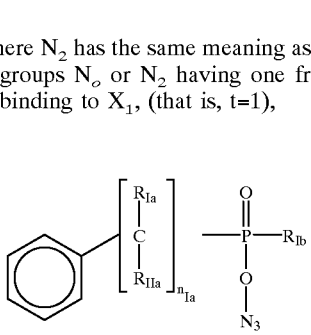

$R_{Ia}$, $R_{IIa}$, $n_{Ia}$ are defined in Ia;

$N_3$ is H, $(CH_3)_2CH-CH-OCOCH_2CH_3$, or a free valence to which $X_1$ binds (that is, $N_3$ is absent);

$R_{Ib}$ is chosen from;

V)

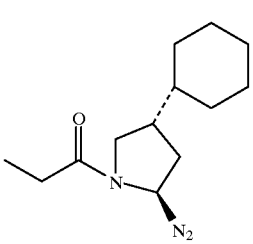

VI)

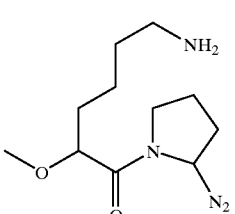

$N_2$ is as above defined, where at least one of the groups $N_3$ or $N_2$ has a free valence capable of binding to $X_1$ (when it is $N_2$, t=1);

$N_2$, t=1);

Ic) where t=1

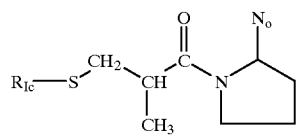

where $N_o$ is as above defined where t=1, i.e. it has a free valence capable of binding to $X_1$;

$R_{Ic}$ is chosen from H, —COCH$_3$, or (VII)

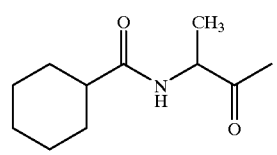

Id)

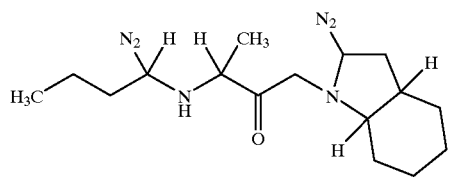

where $N_2$ is as defined, and at least one of the groups $N_2$ has a free valence (t=1) capable of binding to $X_1$;

*Group B
where t=1 and u=0; when Ic/.$R_{IC}$ is H or COCH$_3$, X cannot be NH.

IIa)

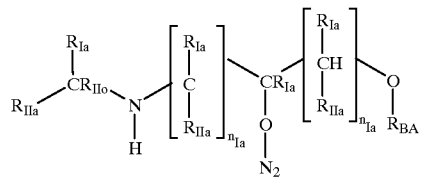

where $R_{Ia}$, $R_{IIa}$ are as defined in Ia);
$R_{IIb}$ has the meaning of $R_{Ia}$;
$R_{BA}$ is chosen from:

L)

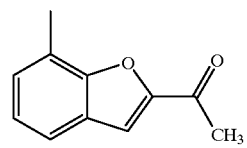

LI)

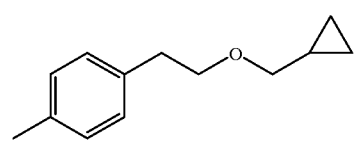

LIII)

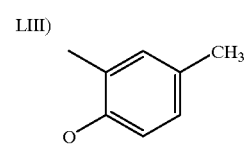

LIII)

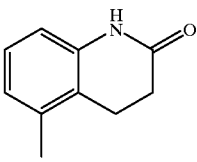

LIV)

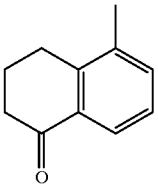

LV)

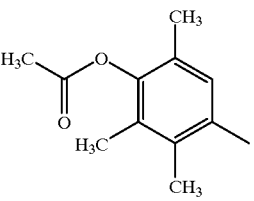

LVI)

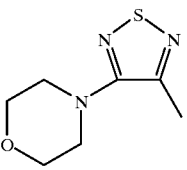

LVII)

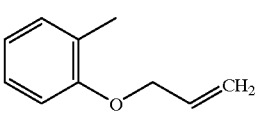

LVIII)

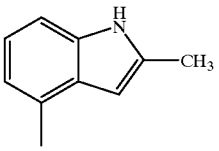

LIX)

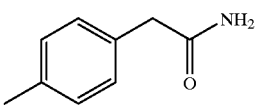

-continued

IIb)

where, in group B), $N_2$ is as above defined and at least one of the $N_2$ groups has a free valence capable of binding to $X_1$, (that is, at least one $N_2$ substituent has t=1;
$X_1$ is a bivalent connecting bridge chosen from the following:
  YO where Y is a linear or whenever possible branched $C_1$–$C_{20}$ alkylene, preferably having from 2 to 5 carbon atoms, or an optionally substituted cycloalkylene having from 5 to 7 carbon atoms;
  $Y_1$ chosen from —(CH$_2$)$_{n3}$—⟨⟩—(CH$_2$)$_{n3}$—O— where $n_3$ is an integer from 0 to 3;

CH$_2$O—
⟨⟩
COOH   CH$_2$—

—(CH$_2$—CH—CH$_2$—O)$_{nf'}$—
           |
          ONO$_2$ where nf' is an integer from 1 to 6, preferably from 2 to 4;

—(CH—CH$_2$—O)$_{nf}$—
  |
  R$_{1f}$ where $R_{1f}$=H, CH$_3$ and nf is an integer from 1 to 6; preferably from 2 to 4.

The compounds which may be mentioned, and which are the preferred compounds, are those listed below where R can be obtained by the processes known in the art.

For example, the compounds and processes described in the Merck Index, Ed. 12 of 1996, an be mentioned as precursors and related processes. The precursors (according to the Merck nomenclature) as those shown below, where the various substituents shown in the formulas of group A) and group B) are as defined in the compounds listed: Alacepril, Benazepril, Captopril, Ceronapril, Cilazapril, Delapril, Enalapril, Enalaprilat Fosinapril, Imidapril, Lisinopril, Quinapril, Ramipril, Spirapril, Temocapril, Trandolapril, Moveltipril, Perindopril, Befunolol, Betaxolol, Bupranolol, Carteolol, Levobunolol, Metipranolol, Timolol, Oxprenolol, Mepindolol, Atenolol, Labetalol.

The connecting bridges $X_1$ as above defined can be obtained using the methods from the known art or modifying the known methods by introducing $X_1$ bridges when these are different from the connecting bridges described in the mentioned patents by processes known in the art. In general, the connection between A and $X_1$ is, as seen, of an ester or amide type (NH or NR$_{1c}$, as defined in X). Any synthetic route well known for forming these bonds can be used.

In the case of esters, the most direct synthetic route includes reaction of acyl chlorides A-CO—Cl, or A-(CO—Cl)$_2$, in halogen alcohols of the type HO—$Y_a$—Cl, HO—$Y_a$—I, where $Y_a$ is equal to Y or $Y_1$ as above defined without the oxygen atom —O—, in experimental conditions which are part of the known art.

The reaction products of formula A-CO—O—$Y_a$—Cl(Br, I) can also be obtained by reacting the sodium or potassium salts of said acids A-CO—OH with di-halogen derivatives of the general formula $Y_a$CL$_2$, $Y_a$Br$_2$ or $Y_a$I$_2$.

The reaction products are converted into the final products by reaction with AgNO$_3$ in acetonitrile according to processes known in the prior art.

The general scheme is as follows:

A-CO—Cl=HO—$Y_a$—Br - - - >A-CO—O—$Y_a$—Br=AgNO$_3$ - - ->A-X$_1$NO$_2$ where $X_1$=$Y_a$O.
  the general scheme can also be as follows:

A-CO—ONa=Br$_2$$Y_a$ - - - >A-CO—O—$Y_a$—Br=AgNO$_3$ - - ->A-X$_1$NO$_2$ where $X_1$=$Y_a$O.

In the case of amides, the synthetic sequence includes reaction of the same acyl chlorides A-CO—Cl with amino alcohols of the general formula NH$_2$—$Y_a$—OH or NHR$_{1c}$—$Y_a$—OH to give amides of the general formula:

A-CO—NH—$Y_a$—OH or A-CO—NR$_{1c}$—$Y_a$OH in accordance with known methods.

Reaction of these amides with halogenating agents such as, for example, PCl$_5$, PBr$_3$, SOCl$_2$, etc, leads to halogen derivatives of the general formula:

A-CO—NH—$Y_a$—Br(Cl) and A-CO—NR$_{1c}$13 $Y_a$—Br(Cl).

By reaction with AgNO$_3$ in acetonitrile according to known literature methods said latter products lead to the final products AX$_1$NO$_2$.

The sequence may be represented as follows:

A—CO—Cl + NHR$_{1c}$—Y$_a$—OH ----▶

A—CO—NR$_{1c}$—Y$_a$—OH $\xrightarrow{PCl_5}$

'A—CO—NR$_{1c}$—Y$_a$—Br + AgNO$_3$ ----▶

A—CO—NR1$_{1c}$—Y$_a$—ONO$_2$ where $Y_a$O is $X_1$.

An alternative route to ester formation is reaction of the sodium or potassium salts of acids with the nitric esters of halogen alcohols of the general formula:

NO$_2$—O—$Y_a$—Cl(Br,I)

to give directly the products of the invention.

The reaction scheme is as follows:

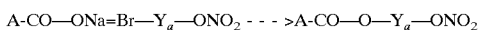

where $Y_aO$ is $X_1$.

Other synthetic routes similar to those described above are the ones where dihalogen derivative $Br_2Y_a$ is reacted with enolates. The reaction products are then converted by reaction with $AgNO_3$ in acetonitrile according to the above reaction. The general scheme shown for an —OH belonging to group A is as follows:

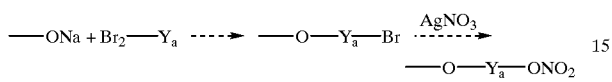

A general method for the —OH group is described in Example 1 only for illustrative purposes.

The processes to obtain these connecting groups $X_1$ are described in patent application WO 95/30641.

The products of the invention as described above are novel as medicaments in general. In particular they are novel for their antithrombotic activity and are also novel as compounds as such.

Additional pharmaceutical uses which can be mentioned for these products of the invention are, for example, their antihypertensive activity (e.g. arterial hypertension, glaucoma) and their cardioprotective activity (e.g. angina pectoris, cardiac failure, coronary ischaemia).

As to antihypertensive activity, it should be noted that the products of the invention showed an extremely satisfactory pharmaco-therapeutic profile with improved efficacy compared to the precursors which do not contain group —$ONO_2$ and, at the same time, showed superior safety.

It should also be noted that the products of the invention exhibit an antihypersensitive activity combined with an antithrombotic activity. This is an outstanding benefit in the treatment of cardiovascular disease in general since the purpose of any therapeutical approach is to ensure to the patient an altogether reduced risk of cardiovascular disease, such as myocardial or cerebral infarction and atherosclerosis (Goodman & Gilman "The pharmacological basis of therapeutics", Ed.J.Hardman, L. Limbrid, pages 747, 1354–7, 1966).

The following examples are being provided as an explanation not a limitation of the present invention.

EXAMPLES

Example 1

Chemical Synthesis and Characterization of NO-timolol (NO-TIM)

Synthesis of (R)-(4-nitroxy)butanoate of 1-[(1,1-dimethyl)amino]-3-{[4-(4-morpholinyl)-1,2,5-thiadiazol-3-yl]oxy}-2-propyl maleate.

The starting point is timolol maleate (a commercial product), the timolol having the general formula:

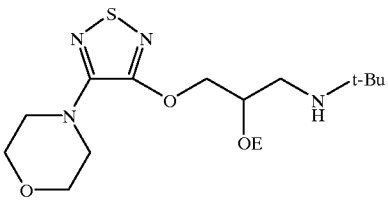

(S)-1-[(1,1-dimethylethyl)amino]-3-{[4-morpholinyl)-1,2,5-thiadiazol-3yl]oxy}-2-propanol.

Timolol maleate (2.0 g) was treated with a solution of 10% NaOH (30 ml). 30 ml of $CH_2Cl_2$ were added and then the phases were separated. The aqueous phase was extracted several times with $CH_2Cl_2$. The pooled organic phases were dried ($Na_2SO_4$) and the solvent evaporated at reduced pressure. 1.4 g of pure product were obtained (yield 96%).

$^1$H NMR (300 MHz $CDCl_3$): δ 1.05 (9H,s,3$CH_3$), 2.7 (2H, 2dd, $CH_2$—NH), 3.5 (4H, m, morpholine), 3,8 (4H, t, morpholine), 3.85 (1H, m, CH), 4.4 (2H, 2dd, O—$CH_2$).

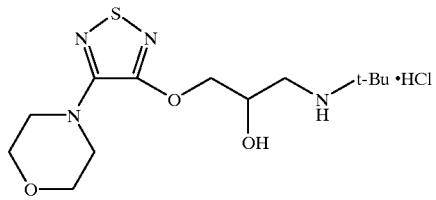

(S)-1-[(1,1-dimethylethyl)amino]-3-{[4-(4-morpholinyl)-1,2,5-thiadiazol-3-yl]oxy}-2-propanol hydrochloride.

0.8 ml of a 7M HCl solution in isopropanol was added dropwise to a magnetically stirred solution of timolol (1.4 g) in isopropanol (30 ml). The solution was stirred for 30 minutes. The reaction mixture was freed of the solvent at reduced pressure. 1.47 g of pure product was obtained (yield 91%).

$^1$H NMR (300 MHz $CDCl_3$): δ 1.45 (9H,s,3$CH_3$), 3.05 (2H, 2dd, $CH_2$—NH), 3.5 (4H,t,morpholine), 3.8 (4H,t, morpholine), 4.5 (2H,d,O—$CH_2$), 4.55 (1H,m,CH).

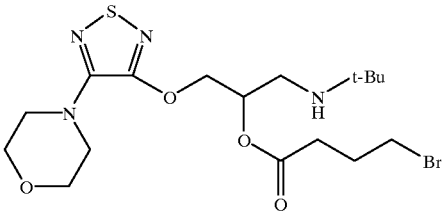

(R)-(4-bromo)butanoate of 1-[(1,1-dimethylethyl)amino]-3-{[4-(4-morpholinyl)-1,2,5-thiadiazol-3-yl]oxy}-2-propyl 4-Bromobutyryl chloride (0.4 ml) was added dropwise in a nitrogen atmosphere to a magnetically stirred solution of timolol hydrochloride (0.82 g) in CHCl$_3$ dried over P$_2$O$_5$ (20 ml). Stirring was continued for 4 days. The reaction mixture was then freed of the solvent at reduced pressure. The residue was chromatographed on silica gel using diethyl ether with 3% Et$_3$N as an eluant. 0.830 g of pure product was obtained from the intermediate fractions (yield 78%).

$^1$H NMR (300 MHz CDCl$_3$):δ 1.05 (9H,s,3-CH$_3$), 2.05 (2H,m,COCH$_2$—CH$_2$—CH$_2$—ONO$_2$), 2.5 (2H,m, COCH$_2$—CH$_2$CH$_2$—ONO$_2$), 2.8 (2H,d,CH$_2$—NH), 3.5 (6H,m,morpholine, CH$_2$—Br), 3.8 (4H,t,morpholine), 4.65 (2H, 2dd, O—CH$_2$), 5.25 (1H,m,CH).

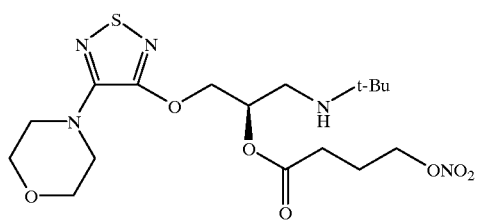

(R)-nitroxy)butanoate of 1-[(1,1-dimethylethyl)amino]-3-{[4-(4-morpholinyl)-1,2,5-thiadiazol-3-yl]oxy}-2-propyl.

A solution of AgNO$_3$ (0.450 g) in CH$_3$CN (5 ml) was added dropwise at ambient temperature to a magnetically stirred solution of timolol (4-bromo)butanoate (0.830 g) in CH$_3$CN (10 ml). The temperature was progressively raised up to 60° C. and reaction was continued for 24 hours. The reaction mixture was freed of the solvent at reduced pressure. The residue was chromatographed on silica gel using diethyl ether with 3% Et$_3$N as an eluant. 0.51 g of pure product was obtained from the first fractions (yield 64%)

$^1$H NMR (300 MHz CDCL$_3$): δ 1.05 (9H,s,3CH$_3$), 2.05 (2H, m,COCH$_2$—CH$_2$—CH$_2$—ONO$_2$), 2.5 (2H, 2t, COCH$_2$—CH$_2$—CH$_2$—ONO$_2$), 2.8 (2H,d,CH$_2$—NH), 3.5 (4H,m,morpholine), 3.8 (4H,t,morpholine), 4.5 (2H,t,—CH$_2$—ONO$_2$), 4.58 (2H, 2dd, O—CH$_2$), 5.25 (1H, m,CH). MS:M$^+$448

(R)-(4-nitroxy)butanoate of 1-[(1,1-dimethylethyl)amino]-3-{[4-(4-morpholinyl)-1,2,5-thiadiazol-3-yl]oxy}-2-propyl maleate.

A solution of maleic acid (0.132 g) in acetone (5 ml) was added dropwise to a magnetically stirred solution of timolol (4-nitroxy)butanoate (0.50 g) in acetone (10 ml). Stirring was continued for 2 hours. The reaction mixture was freed of the solvent at reduced pressure. The crude residue was grounded with diethyl ether to give 0.5 g of a white solid (m.p. 133–136° C., yield 70%)

$^1$H NMR (300 MHz CDCl$_3$): δ 1.48 (9H,s,3CH$_3$), 2.05 (2H,m,— COCH$_2$—CH$_2$—CH$_2$—ONO$_2$), 2.58 (2H, 2td, COCH$_2$—CH$_2$—CH$_2$—ONO$_2$), 3.3 (2H,2m, CH$_2$—NH$_2$), 3.5 (4H, m, morpholine), 3.8 (4H, t, morpholine), 4.5 (2H, t, CH$_2$—ONO$_2$) 4.7 (2H, 2dd, O—CH$_2$), 5.55 (1H, m, CH), 6.47 (2H, s, maleic)

Example 2A

Chemical Synthesis and Characterization of NO-enalapril (NO-ENA)

The reaction scheme is as follows:

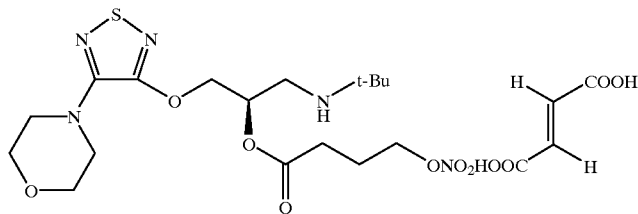

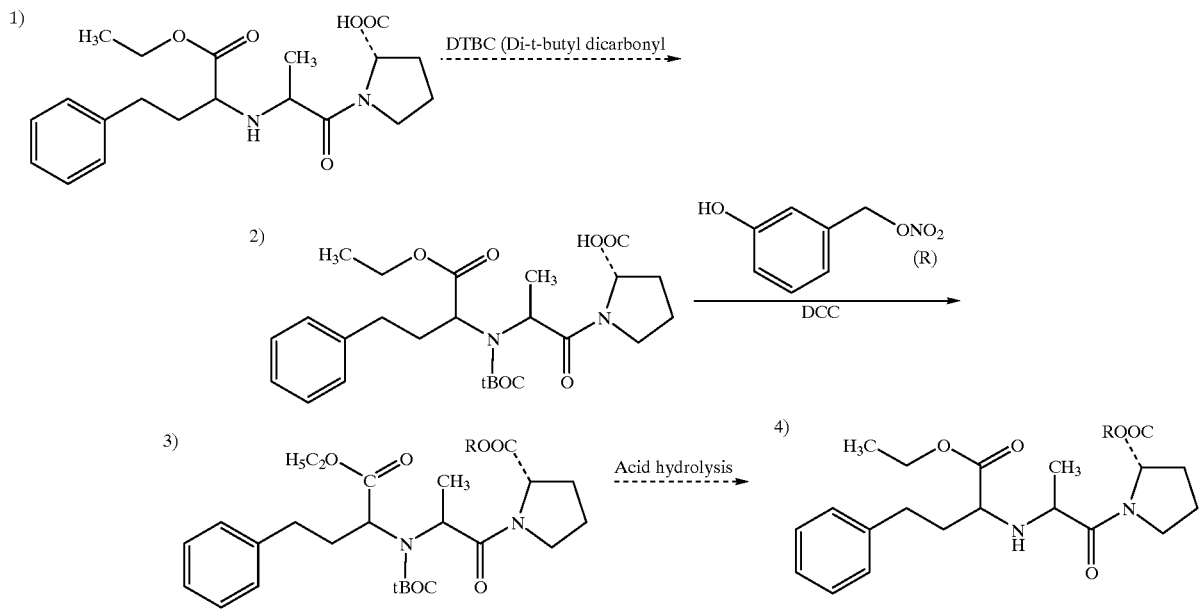

Step 1

3 g of diterbutyldicarbonyl (DTBC) was added at ambient temperature to a solution of 5 g of enalapril in 100 ml of dimethylformamide (DMF) and triethylamine (TEA) (2.76 g). The solution was stirred for 16 hours. Then the solution was washed twice with diluted HCl and water, extracted 3 times with 100 ml portions of ether. The dried and evaporated-off organic phases gave 3 g of a formula 2) product (an oil). In formula 2) tBOC=t-butyldicarbonyl.

Step 2

1.4 g of dicyclohexyl carbodiimide (DCC), and then 30 ml of a solution of 1.1 g of nitroxymethylphenol in $CH_2Cl_2$, were added to 3 g of N-protected enalapril (a compound of formula 2) dissolved in 50 ml of methylene dichloride. The mixture was stirred overnight, dicyclohexylurea was filtered off and the solvent was evaporated off the dryness. The residue was chromatographed on silica gel 60 Merck using an ethyl acetate/hexane mixture. A fraction of 2 g of intermediate of formula 3), where R was the residue of nitroxymethylphenol without OH, was collected.

Step 3

1 g of the product of formula 3) was dissolved at 0° C. in a 4N solution of 30 ml of dry HCl gas in ethyl acetate (ACO-ET) and stirred for 10 hours. The precipitate obtained was filtered and dried under vacuum 0.5 g of a product 4) was obtained.

Example 25

Chemical Synthesis and Characterisation of NO-enalaprilate (NO-ENP)

The reaction scheme is as follows:

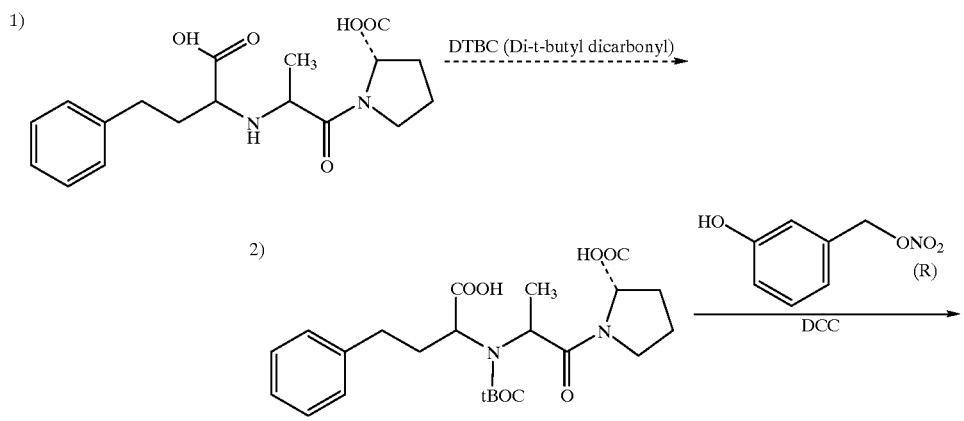

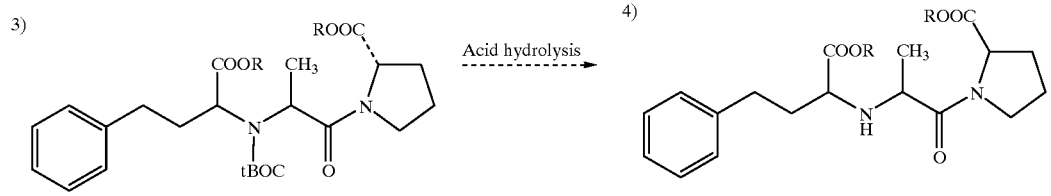

Step 1:

3 g of diterbutyldicarbonyl (DTBC) was added at ambient temperature to a solution of 5 g of enalaprilate in 100 ml of dimethylformamide (DMF) and triethylamine (TEA) (2.76 g). The solution was stirred for 16 hours. Then the solution was washed twice with diluted HCl and water, extracted 3 times with 100 ml portions of ether. The dried and evaporated-off organic phases gave 3 g of a product 2) as an oil. In formula 2) tBOC=t-butyldicarbonyl.

Step 2:

2.75 of dicyclohexyl carbodiimide (DCC), and then 30 ml of a solution of 2.25 g of nitroxymethylphenol, were added to 3 g of N-protected enalaprilate dissolved in 50 ml of methylene dichloride. The mixture was stirred overnight, dicyclohexylurea was filtered off and the solvent was evaporated off to dryness. The residue was chromatographed on silica gel 60 Merck using an ethylacetate/hexane mixture. A fraction of 3 g of intermediate product 3) was collected. R has the meaning as defined in Example 2A.

Step 3:

1 g of product 3) was dissolved at 0° C. in a 4N solution of 30 ml of dry HCl gas in ACOEt and stirred for 10 hours. The precipitate obtained was filtered and dried under vacuum. 0.7 g of a product 4) was obtained.

Example 3:

Pharmacological Studies

The products from Examples 1 and 2 had been administered in vivo always as 2%-by-weight suspensions in carboxymethyl cellulose.

The experimental groups were made up of 6 to 8 samples to allow appropriate statistical evaluation, which was carried out when needed.

As far as acute toxicity for the compounds which are the object of the invention, it was evaluated after a single oral dose to groups of 10 mice each.

Death rate and presence of toxic symptoms were recorded during an observation period of 14 days. Even after a 50 mg/kg dose the animals showed no sign of apparent overt toxicity.

Example 3A

Study of Antiplatelet Activity

The ability of NO-ENA and NO-TIM to inhibit platelet aggregation was evaluated using an in vivo model as described by Pinon (J. Pharmacol. Methods 12,79,1989). 5 groups of male Wistar rats (200 to 250 g) received an oral daily dose of 10 mg/kg of respectively, NO-ENA, enalapril, NO-TIM, timolol or vehicle for 5 days. At an appropriate time on the forth day food (but not water) was withdrawn. 18 to 20 hours later the animals received the last treatment. One hour later the animals were anaesthetized with 10% urethane (1 mg/kg intraperitoneally) and the left jugular vein and right carotid artery were incannulated. Collagen (type 6, Sigma) was then administered intravenously at a dose of 2 mg/kg. Three minutes later two blood samples (A and B) were collected from the carotide artery using 2.5-ml plastic syringes in the following manner: sample A, 0.4 ml of blood in 1.6 ml of EDTA/formalin buffer (ETDA tetrasodium salt 24 mM, $KH_2PO_4$ 1.3 mM, $Na_2PO_4$ 13.4 mM), the samples were then transferred into 5-ml polystyrene test tubes and allowed to settle for 15 minutes at ambient temperature. After this time, the platelet aggregations in sample A were fixed in formalin, while those from sample B were treated with EDTA. Platelet count was then made in each sample using a conventional microscope. The count for sample B was the total number of platelets, while for sample A were considered only non-aggregated platelets. The results were expressed as per-cent aggregation, calculated as follows: {[1-(platelet count in sample A)/(platelet count in sample B)]×100}. The results were expressed as per-cent inhibition of the control group (vehicle) and shown in Table 1.

TABLE 1

STUDY OF ANTIPLATELET ACTIVITY OF NO-ENA OR NO-TIM VERSUS ENALAPRIL OR TIMOLOL IN RATS

| COMPOUND | ANTIPLATELET ACTIVITY (%) |
|----------|---------------------------|
| NO-ENA   | 65 |
| NO-TIM   | 58 |
| ENALAPRIL | 15 |
| TIMOLOL  | 2 |

As shown in Table 1, differently from the reference products, the nitroderivatives of the invention were able to inhibit aggregation induced by collagen.

Example 3B

Study of Antithrombotic Activity 5 groups of male Charles River rats of the Swiss strain, 15 to 20 g, received a daily oral dose of 10 mg/kg of, respectively, NO-ENA, enalapril, NO-TIM, timolol or vehicle for 5 days. At an appropriate time on the fourth day food (but not water) was withdrawn. 18 to 20 hours later the animals received the last treatment. One hour later the animals were injected into the caudal vein with 0.1 ml of a collagen (type 6, Sigma) mixture plus adrenaline hydrochloride (100 $\mu$M) diluted in a solution of 0.154 M sodium chloride. As previously explained (Cirino G. et al., Thrombosis Reasearch 79, 73, 1995), injection of this mixture caused death within 3 minutes in 90% of the control animals.

The results were expressed as inhibition percentage compared to the control group and are shown in Table 2.

TABLE 2

STUDY OF ANTITHROMBOTIC ACTIVITY OF NO-ENA OR NO-TIM VERSUS ENALAPRIL OR TIMOLOL IN RATS

| COMPOUND | ANTITHROMBOTIC ACTIVITY (%) |
|---|---|
| NO-ENA | 53 |
| NO-TIM | 44 |
| ENALAPRIL | 11 |
| TIMOLOL | 6 |

As shown in Table 2, differently from the reference products, the nitroderivatives of the invention were able to inhibit thrombosis induced by collagen.

Example 3C

Study of Antihypertensive Activity

The ability of NO-ENA to inhibit hypertension was evaluated using an in vivo model as described by Ribeiro et al. (Hypertension 20, 298, 1992). 5 groups of male Wistar rats (235 to 284 g) received a daily intravenous dose of 10 mg/kg of, respectively, NO-ENA, enalapril, NO-TIM, timolol or vehicle for 5 days. Arterial hypertension was induced by administration of $N^w$-nitro-L-argininemethyl ester (L-NAME) in the drinking water for 6 weeks. L-NAME was dissolved in the drinking water at a concentration of 60 to 70 mg 100 ml$^{-1}$ so as to administer a daily amount of about 60 mg kg$^{-1}$. One hour after treatment the systemic blood pressure was measured by the tail-cap method (Zats, Lab. Anim. Sci.42, 198, 1990).

TABLE 3

STUDY OF ANTIHYPERTENSIVE ACTIVITY OF NO-ENA VERSUS ENALAPRIL IN RATS

| COMPOUND | MEAN BLOOD PRESSURE (mmHg) |
|---|---|
| VEHICLE | 170 ± 7 |
| NO-ENA | 115 ± 4* |
| ENALAPRIL | 163 ± 5 |

*P < 0.05 versus the other two groups

As shown by Table 3, differently from the reference product, the nitroderivative of the invention was able to inhibit blood hypertension induced by thrombosis induced by L-NAME.

Example 3B

Study of Ocular Hypotensive Activity and Ocular Safety of NO-ENA or NO-TIM Versus Enalapril or Timolol in Rabbits In rabbits, the topical application of 100 μg of NO-ENA or NO-TIM gave a more pronounced and more lasting (more than 6 hours) reduction of intraocular pressure (6–7 mmHg respectively) than the reference products timolol and enalapril. Furthermore, for NO-TIM, the ratio between product concentrations in plasma (P) and aqueous humor (AH) versus timolol was determined by an HPLC method. It was found that the P/AH ratio for NO-TIM was 5.5 times lower than that for timolol, suggesting that the systemic absorption of the nitroderivative (and consequently any potential side effect from said derivative) was markedly reduce compared to the reference product.

Example 3E

Study of NO-ENA Effects on Induced Bronchoconstriction in Guinea Pigs Versus Enalapril Bronchoconstriction induced by capsaicin in Guinea pigs is an animal model related to the ability of ACE (angiotensin-converting enzyme) inhibitors to cause cough in patients (Subissi et al., J. Cardiovasc. Pharmacol.20/1, 139–146, 1992).

Adopted test conditions were as previously described by Del Soldato et al. (J. Pharmacological Methods 5, 279, 1981). Female Guinea pigs weighing 300 to 400 g were anaesthetised by intraperitoneal injection of sodium 5,5-diethylbarbiturate (200 mg/kg) and maintained under artificial respiration at constant positive pressure. The right jugular vein was incannulated for administering test compound. By a median incision of the abdomen, the duodenum was removed and through a small incision the tip of a suitable polyethylene cannula was inserted and fixed. The other end of the cannula was connected to a syringe for intraduodenal administration of NO-ENA (10 mg/kg), enalapril (10 mg/kg) or vehicle. 45 minutes later, 0.1 ml of capsaicin (1 μg/kg) was injected into the jugular vein of the animals. Before and after injection of capsaicin, changes in the tidal area were measured by a modified Konzett apparatus connected to a suitable polygraphic amplifier (Hewlett Packard).

The results were calculated as the ratio of the responses obtained before and after administration of the test compound, expressed as a % of the response obtained with the vehicle alone, shown in Table 4.

TABLE 4

STUDY OF EFFECTS OF NO-ENA ON BRONCHOCONSTRICTION INDUCED IN GUINEA PIGS VERSUS ENALAPRIL

| TREATMENT | BRONCHOCONSTRICTIVE RESPONSE (%) |
|---|---|
| VEHICLE | 100 |
| NO-ENA | 72 |
| ENALAPRIL | 327 |

As shown in Table 4, the nitroderivative of the invention reduced bronchoconstriction induced by capsaicin differently from the reference product, which actually markedly enhanced the bronchoconstrictive response.

CONCLUSIONS

As can be observed from the above examples, the nitroderivatives which are an object of the present invention show marked antithrombotic and cardiovascular activity with excellent safety when compared to reference products.

What is claimed is:

1. Compounds, or their compositions, of the general formula:

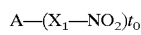

$$A-(X_1-NO_2)_{t_0}$$

or their salts, where:

$t_0$ is an integer equal to 1 or 2;

$A=RN_0$ where $N_0=(COX_u)_t-$ or $COON_1$ where t is an integer equal to zero or 1; u is an integer equal to 0 or 1;

X=O, NH, $NR_{1c}$ where $R_{1c}$ is a linear or branched alkyl having from 1 to 10 carbon atoms; $N_1$ is a linear or branched alkyl having from 1 to 10 carbon atoms or hydrogen;

R is chose from the following groups:

Group A)

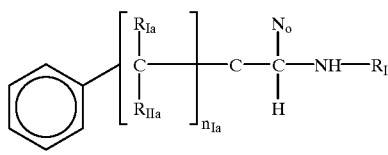

where
where $R_{Ia}$ and $R_{IIa}$ are equal or different one from the other and are H or a linear or whenever possible branched alkyl from 1 to 3 C atoms, preferably $R_{IA}=R_{IIa}=H$; $n_{Ia}$ is an integer from 1 to 6, preferably from 2 to 4;
$R_I$ can be:

(X)

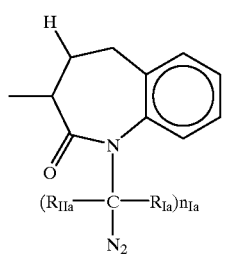

(XI)

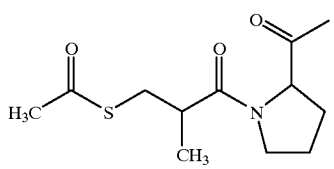

(XII)

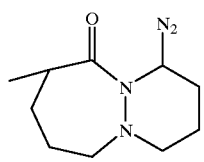

(XIII)

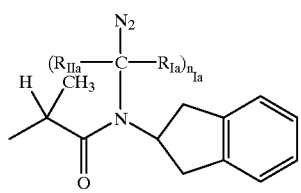

(XIV)

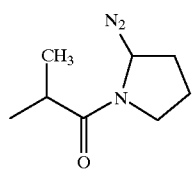

(XV)

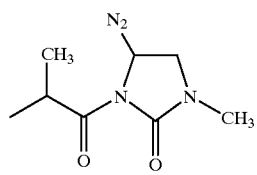

(XVI)

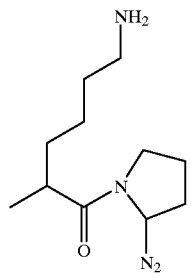

(XVII)

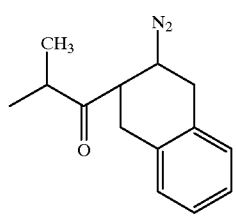

(XVIII)

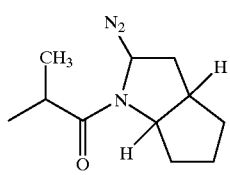

(XIX)

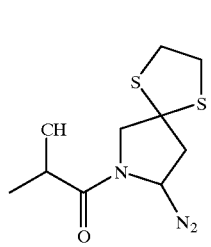

(XX)

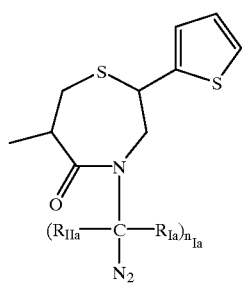

(XXI)

where $N_2$ has the same meaning as $N_0$; at least one of the groups $N_0$ or $N_2$ having one free valence capable of binding to $X_1$ (that is, t=1), Ib)

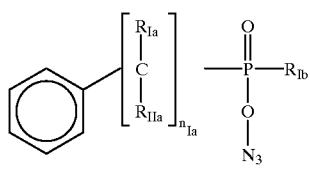

$R_{Ia}$, $R_{IIa}$, $n_{Ia}$ are as defined in Ia;
$N_3$ is H,

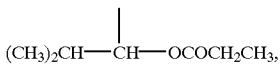

or a free valence to which $X_1$ binds (that is, $N_3$ is absent);
$R_{Ib}$ is chosen from:

V)

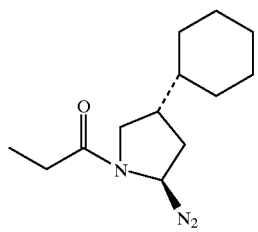

VI)

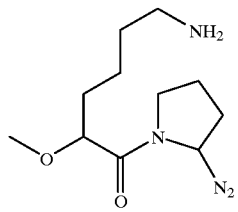

$N_2$ is as above defined, where at least one of the groups $N_3$ or $N_2$ has a free valence capable of binding to $X_1$ (when it is $N_2$, $t=1$);

Ic) where t = 1

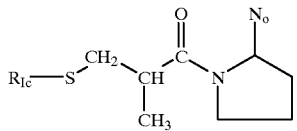

where $N_0$ is as above defined where $t=1$, i.e., it has a free valence capable of binding to $X_1$;
$R_{Ic}$ is chosen from H, —COOH$_3$, or (VII)

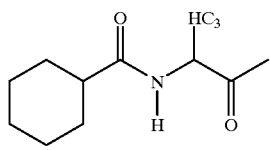

Id)

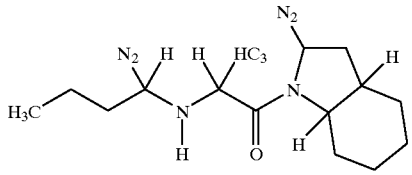

where $N_2$ is as defined, and at lest one of the groups $N_2$ has a free valence (t=1) capable of binding to $X_1$, with the proviso that when in group Ic) $R_{IC}$ is H or COCH, X cannot be NH;

Group B
  where t=1 and u=0;

IIa)

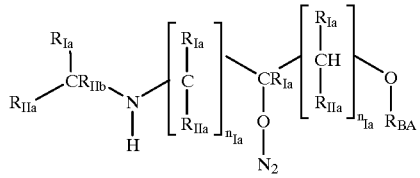

where $R_{Ia}$, $R_{IIa}$ are as defined in Ia);
$R_{IIb}$ has the meaning or $R_{Ia}$;
$R_{BA}$ is chosen from:

L)

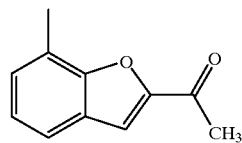

LI)

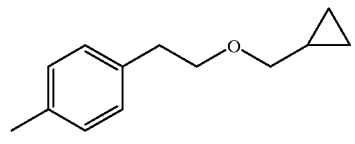

LII)

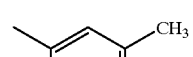

LIII)

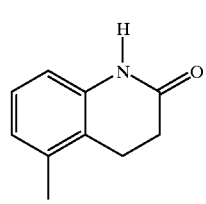

LIV)

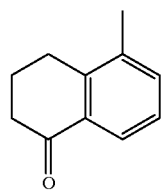

LV) 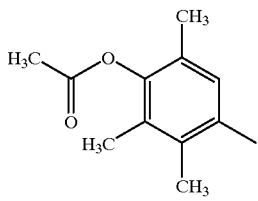

LVI) 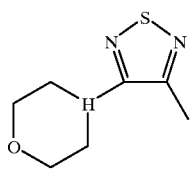

LVII) 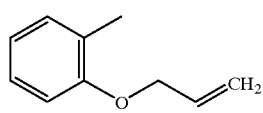

LVIII) 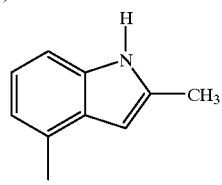

LIX) 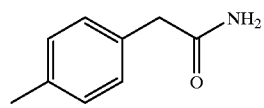

IIb) 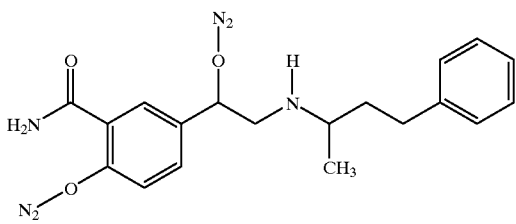

where in group B), $N_2$ is as above defined and at least one of the $N_2$ groups has a free valence capable of binding to $X_1$, (that is, at least one $N_2$ substituent has t=1);

$X_1$ is bivalent connecting bridge chosen from the following:

YO where Y is linear or whenever possible branched $C_1$–$C_{20}$ alkylene, preferably having from 2 to 5 carbon atoms, or an optionally substituted cycloalkylene having from 5 to 7 carbon atoms;

$Y_1$ chosen from

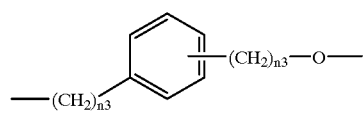

where $n_3$ is an integer from 0 to 3;

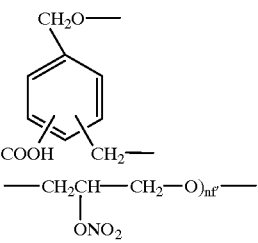

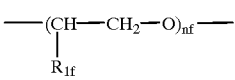

where nf' is an integer from 1 to 6;

$$—(CH—CH_2—O)_{nf}—$$
$$\phantom{—(}R_{1f}$$

where $R_{1f}$=H, $CH_3$ and nf is an integer from 1 to 6.

2. Compounds according to claim 1, in which R, $R_I$, $R_{Ib}$, $R_{Ic}$, $R_{BA}$ and compounds Id) and IIb) are the residues of Alacepril, Benazepril, Captopril, Ceronapril, Cilazapril, Delapril, Enalapril, Enalaprilat, Fosinapril, Imidapril, Lisinopril, Quinapril, Ramipril, Spirapril, Temocapril, Trandolapril, Moveltilpril, Perindopril, Befunolol, Betaxolol, Bupranolol, Carteolol, Levobunolol, Metipranolol, Timolol, Oxprenolol, Mepindolol, Atenolol, Labetalol.

3. Compounds according to claim 1, in which $X_1$ is chosen from

YO where Y is a linear or whenever possible branched $C_1$–$C_{20}$ alkylene, preferably having from 2 to 5 carbon atoms, or an optionally substituted cycloalkylene having from 5 to 7 carbon atoms;

$Y_1$ chosen from

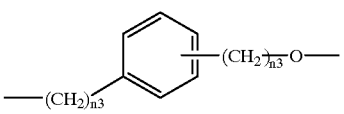

where $n_3$ is an integer from 0 to 3.

4. A pharmaceutically acceptable composition comprising the compound of claim 1 and a pharmaceutically acceptable carrier.

5. A pharmaceutically acceptable composition comprising the compound of claim 1 and a pharmaceutically acceptable carrier.

6. A pharmaceutically acceptable composition comprising the compound of claim 3 and a pharmaceutically acceptable carrier.

7. A method for treating thrombosis comprising administering to a patient in need thereof a therapeutically effective amount of a composition comprising the compound of claim 1.

8. A method for treating thrombosis comprising administering to a patient in need thereof a therapeutically effective amount of a composition comprising the compound of claim 2.

9. A method for treating thrombosis comprising administering to a patient in need thereof a therapeutically effective amount of a composition comprising the compound of claim 3.

10. A method for treating hypertension comprising administering to a patient in need thereof a therapeutically effective amount of a composition comprising the compound of claim 1.

11. A method for treating hypertension comprising administering to a patient in need thereof a therapeutically effective amount of a composition comprising the compound of claim 2.

12. A method for treating hypertension comprising administering to a patient in need thereof a therapeutically effective amount of a composition comprising the compound of claim 3.

13. A method for treating heart disease comprising administering to a patient in need thereof a therapeutically effective amount of a composition comprising the compound of claim 1.

14. A method for treating heart disease comprising administering to a patient in need thereof a therapeutically effective amount of a composition comprising the compound of claim 2.

15. A method for treating heart disease comprising administering to a patient in need thereof a therapeutically effective amount of a composition comprising the compound of claim 3.

* * * * *